(12) United States Patent
Cole et al.

(10) Patent No.: US 7,314,760 B2
(45) Date of Patent: Jan. 1, 2008

(54) BIOCHEMICAL TEST FOR IDENTIFYING PREGNANCIES WITH DOWN'S SYNDROME FETUS

(75) Inventors: Laurence A Cole, Albuquerque, NM (US); Jaime M Riley, Albuquerque, NM (US)

(73) Assignee: STC. UNM, Albuquerque, NM (US)

( * ) Notice: Subject to any disclaimer, the term of this patent is extended or adjusted under 35 U.S.C. 154(b) by 0 days.

(21) Appl. No.: 10/862,791

(22) Filed: Jun. 7, 2004

(65) Prior Publication Data
US 2004/0253626 A1 Dec. 16, 2004

Related U.S. Application Data

(60) Provisional application No. 60/477,287, filed on Jun. 10, 2003.

(51) Int. Cl.
*G01N 33/48* (2006.01)
*G01N 33/50* (2006.01)
*A61K 38/24* (2006.01)

(52) U.S. Cl. .......................... 436/87; 435/7.1; 530/399

(58) Field of Classification Search .................. 435/7.1
See application file for complete search history.

(56) References Cited

U.S. PATENT DOCUMENTS

| | | | |
|---|---|---|---|
| 5,324,667 A | 6/1994 | Macri | |
| 6,025,149 A | 2/2000 | Cuckle et al. | |
| 6,429,018 B1 | 8/2002 | Cole et al. | |
| 6,500,627 B1 | 12/2002 | O'Connor et al. | |
| 2003/0027234 A1 | 2/2003 | Pandian et al. | |

FOREIGN PATENT DOCUMENTS

WO     WO 98/10282     * 3/1998

OTHER PUBLICATIONS

Cole et al., Prenat. Diagn 1997, vol. 17, pp. 1188-1190.*
Cole et al., Prenat. Diagn 1999, vol. 19, pp. 351-359.*
Sutton et al., Prenat Diagn. 2004, vol. 24(3): pp. 194-197.*
Alfthan et al., Mol Cell Endocrinol. 1996, vol. 125(1-2): pp. 107-120.*
Cole, Laurence A. et al., "Hyperglycosylated Human Chorionic Gonadotropin (Invasive Trophoblast Antigen) Immunoassay: A New Basis for Gestational Down Syndrome Screening," Clin. Chem., 1999, 45:12, 2109-19.
ABSTRACT: Cuckle, H. S. et al., "Maternal Urine Hyperglycosylated hCG in Pregnancies With Down Syndrome," Prenat. Diag., Oct. 1999, 19(10), 918-20.
ABSTRACT: Bahado-Singh, R. et al., "Urine Hyperglycosylated hCG Plus Ultrasound Biometry for Detection of Down Syndrome in the Second Trimester in a High-risk Population," Obstet. Gynecol., Jun. 2000, 95(6, pt. 1), 889-94.
ABSTRACT: Bahado-Singh, R. et al., "Comparison of Urinary Hyperglycosylated Human Chorionic Gonadotropin Concentration with the Serum Triple Screen for Down Syndrome Detection in High-risk Pregnancies," Am. J. Obstet. Gynecol., Nov. 2000, 183(5), 1114-18.

* cited by examiner

*Primary Examiner*—Lorraine Spector
(74) *Attorney, Agent, or Firm*—Henry D Coleman; R. Neil Sudal; William J Sapone

(57) ABSTRACT

The invention provides prenatal screening methods for Down's syndrome. Specifically, the methods of the invention comprise determining the amount of hyperglycosylated human chorionic gonadotropin (hCG) charge isoforms in a biological sample from a pregnant woman and comparing the amount of highly acidic and less acidic isoforms with those found in a sample taken from a pregnant woman carrying a normal fetus. The methods of the invention can be employed during any stage of pregnancy.

2 Claims, 4 Drawing Sheets

BIOCHEMICAL TEST FOR IDENTIFYING PREGNANCIES WITH DOWN'S SYNDROME FETUS

RELATED APPLICATIONS

This application claims the benefit of priority of application 60/477,287, filed Jun. 10, 2003, the entire contents of which are incorporated by reference herein.

GOVERNMENT SUPPORT

This application was supported by a grant from the National Institutes of Health; grant number HD-35654. The U.S. government may have certain rights to this invention.

FIELD OF THE INVENTION

The invention relates to methods for detecting the presence or absence of Down's syndrome in a fetus of a pregnant woman.

BACKGROUND OF THE INVENTION

Down's syndrome, also referred to as trisomy 21, is characterized by an extra copy of chromosome 21. People afflicted with Down's syndrome have severe mental retardation, reduced life expectancies, and abnormal immune responses that predispose them to serious infections as well as thyroid autoimmunity. Further, 40% of Down's syndrome patients have congenital heart disease and a 10 to 20-fold increased risk of developing leukemia relative to the general population. All Down's syndrome patients older than 40 develop neuropathological changes that are characteristic of Alzheimer's disease.

Prenatal tests to detect aneuploidy, such as trisomy 21, by amniocentesis or chorionic villus sampling (CVS) have been available since the late 1960s. Amniocentesis is the most common invasive prenatal diagnostic procedure. In amniocentesis, amniotic fluid is sampled by inserting a hollow needle through the mother's anterior abdominal and uterine walls into the amniotic cavity by piercing the chorion and amnion. It is usually performed in the second trimester of pregnancy. CVS is performed primarily during the first trimester, and involves collecting cells from the chorion which develops into the placenta.

Another invasive prenatal diagnostic technique is cordocentesis or percutaneous umbilical cord blood sampling, commonly known as fetal blood sampling. Fetal blood sampling involves obtaining fetal blood cells from vessels of the umbilical cord, and is performed about the 20th gestational week.

Amniocentesis is used selectively because it presents a risk of about 1% of inducing spontaneous abortion. CVS and fetal blood sampling carry a similar or higher risk of inducing abortion, and there is also concern that these procedures may lead to fetal limb malformations in some cases. Thus, amniocentesis, CVS and fetal blood sampling are procedures that are only employed if a pregnancy is considered at high risk for a serious congenital anomaly. Thus, some means is required to select those pregnancies that are at a significant risk of Down's syndrome to justify the risks associated with invasive prenatal diagnostic procedures, such as amniocentesis, CVS and fetal blood sampling.

Human chorionic gonadotropin (hCG) is a glycoprotein with 8 oligosaccharide side chains. Sugar residues account for approximately 30% of the molecular weight of hCG, and variation in oligosaccharide branching is a key factor in the hCG structure (Elliott et al., 1997, *Endocrine* 7:15-32). hCG exists in maternal urine in various forms including hyperglycosylated hCG, also called invasive trophoblastic antigen (ITA). While hCG is produced by differentiated syncytiotrophoblast cells, ITA is produced solely by invasive cytotrophoblast cells (Kovalevskaya et al., 2002, *Mol Cell Endocrinol* 194:147-55; Lei et al., 1999, *Troph Res* 13:147-59). ITA, which is the predominant form of hCG produced in invasive trophoblast disease and early pregnancy at the time of and following implantation, contains additional antennae on the oligosaccharide side chains (O'Connor et al., 1998, *Prenat Diagn* 18:1232-40). Each of the side chain antennae normally ends with a sialic acid residue. The extent of sialic acid content on the ITA molecule is dependent on abundance of sialic acid in the body. Phosphoenolpyruvate, which is a major intermediate in sugar metabolism, is a substrate in the production of sialic acid (Elliott et al., 1997, *Endocrine* 7:15-32). Thus, depending on cellular growth and metabolism, ITA can vary greatly in sialic acid content, or charge; it is generally more deficient in this acidic sugar than is hCG (Elliott et al., 1997, *Endocrine* 7:15-32). Normally-glycosylated hCG contains between 11 and 15 sialic acid residues, whereas ITA can contain between 8 and 19 sialic acid residues (Elliott et al., 1997, *Endocrine* 7:15-32). Sialic acid contributes to the biological activity of the molecule by protecting terminal galactose residues from liver galactose receptors, by increasing the circulating half-life of the molecule, and by stabilizing the hCG $\alpha$-$\beta$ dimer (Brand et al., 1980, *Acta Endocrinologica* 95:75-83; Rosa et al., 1984, *J Clin Endocrinol Metab* 59:1215-9; Van Hall et al., 1970, *Endocrinology* 89:11-15).

Increased proportions of ITA are produced in Down syndrome pregnancies (Cole et al., 1999, *Clin Chem* 45:2109-19). This is due to the failure of trophoblast cells to differentiate into syncytiotrophoblasts, leading to an accumulation of invasive cytotrophoblast cells in these pregnancies (Evain-Brion et al., 2000, *Bull Acad Natl Med* 184:1033-45; Frendo et al., 2000, *J Clin Endocrinol Metab* 85:3700-7; Massin et al., 2001, *Placenta* 22:S93-97).

Previous reports have demonstrated that ITA can be used as a marker for Down's syndrome pregnancies in the first and second trimester (Cole et al., 1998, *Prenat Diagn* 18:926-33; Cole et al., 1999, *Clin Chem* 45:2109-19; Cuckle et al., 1999, *Prenat Diagn.* 19:911-7; Strom et al., 2001, 51st Annual Meeting of the American Society of Human Genetics, San Diego, Calif., (Abstract 2839); Weinans et al., 2000, *Prenat Diagn* 20:976-8). One urine-based ITA study reports detecting 80% of Down syndrome cases with a 5% false-positive rate in the second trimester of pregnancy (Cole et al., 1999, *Clin Chem* 45:2109-19). In addition, when ITA was used in combination with the triple screen test (measures total hCG, unconjugated estriol, and $\alpha$-fetoprotein), an even higher sensitivity marker was attained, detecting 96% of cases with a 5% false positive rate, or 94% of cases at a 3% false positive rate (Cole et al., 1999, *Clin Chem* 45:2109-19). A serum-based ITA study reported detecting 92% of Down syndrome cases with a 3% false positive rate (Lee et al., 2001, 51$^{st}$ Annual Meeting of the American Society of Human Genetics, San Diego, Calif., Abstract 160). First-trimester clinical trials indicated 60% detection of Down syndrome cases with a 5% false positive rate when using PAPP-A and hCG free-$\beta$ subunit; however the addition of an ITA measurement raised the detection level to 81% with a 5% false positive rate (Strom et al., 2001, 51st Annual Meeting of the American Society of Human Genetics, San Diego, Calif., Abstract 2839).

Therefore, while screens that include detecting of ITA are vast improvements over previously used screening methods, increasing the positive rate and decreasing the false positive rate of the tests is desirable, particularly in the first trimester.

SUMMARY OF THE INVENTION

The invention provides non-invasive, prenatal screening tests for Down's syndrome pregnancies.

In one aspect, the invention provides a method for detecting the presence or absence of Down's syndrome in a fetus of a pregnant woman comprising the steps of: (a) obtaining a biological sample from a pregnant woman; and (b) measuring an amount of less acidic hCG isoforms present in the biological sample and comparing the amount of less acidic hCG isoforms with a predetermined value, whereby the amount of less acidic hCG isoforms relative to the predetermined value indicates the presence or absence of Down's syndrome in the fetus.

In one embodiment, the method further comprises measuring an amount of highly acidic hCG isoforms in the biological test sample; and calculating the ratio of the amount of the less acidic hCG isoforms to the amount of the highly acidic isoforms of hCG, whereby the presence of Down's syndrome is detected if the ratio of less acidic to highly acidic isoforms of hCG is about 1.5 or higher. The amount of highly acidic hCG isoforms can comprise normal hCG.

In another embodiment, a "biological sample" is urine, saliva, serum, plasma, tears, or amniotic fluid.

In yet another embodiment, the amount of highly acidic or less acidic hCG isoforms can be detected by isoelectric focusing; immunoassays using antibodies specific for hCG, hCG subunits, or particular hCG isoforms, or a combination thereof; carbohydrate analysis, such as using a lectin specific for the carbohydrate portion of Down's syndrome hCG (see, for example, U.S. Pat. No. 6,429,018, which is hereby incorporated by reference); or some combination of isoelectric focusing, immunoassays, and carbohydrate analysis.

Specific preferred embodiments of the present invention will become evident from the following more detailed description of certain preferred embodiments and the claims.

DETAILED DESCRIPTION OF PREFERRED EMBODIMENTS

Figure 1:
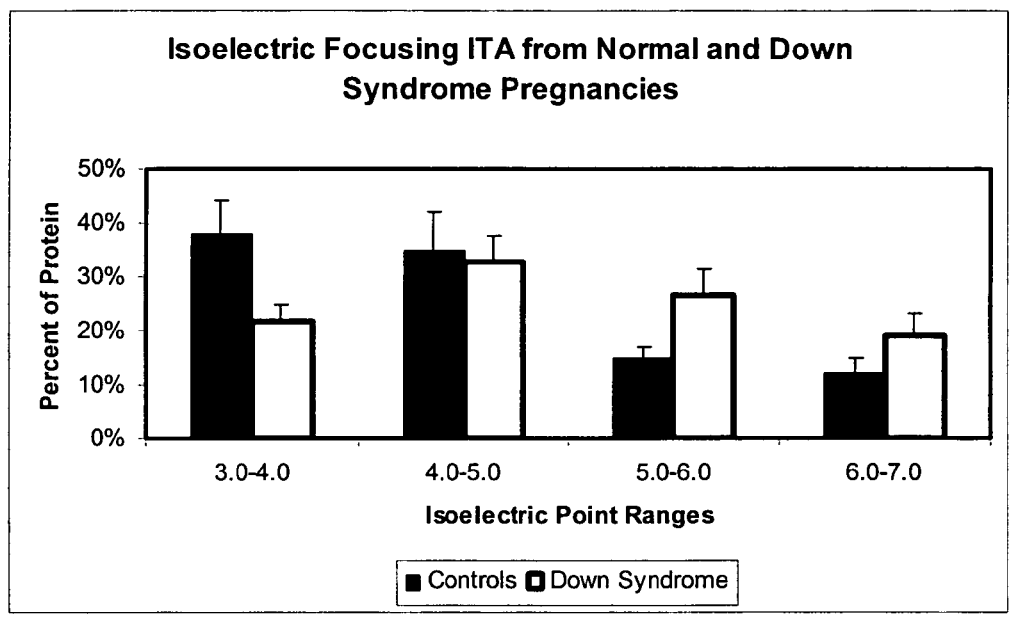
FIG. 1 shows the charge distribution of ITA from normal and Down syndrome urine samples in the pI ranges of about 3-4,4-5, 5-6, and 6-7.

As used herein, "hCG" is an abbreviation for human chorionic gonadotropin, a glycoprotein hormone secreted in relatively large quantities by the trophoblast cells of the placenta. hCG, also referred to herein as "normal hCG," is composed of two dissimilar subunits, α (92 amino acids and two N-linked oligosaccharides) and β (145 amino acids and two N-linked and four O-linked oligosaccharides), joined noncovalently, and is detected in the serum and urine of pregnant women and in those with trophoblast disease (such as hydatidiform mole or choriocarcimoma). Free α- and free β-subunits are also detected in serum and urine samples.

As used herein, "ITA" is an abbreviation for invasive trophoblast antigen, also known as hyperglycosylated gonadotropin, having sialic acid residues up to 20. In addition, "ITA-2," as used herein, refers to invasive trophoblastic antigen-2, which is a less acidic isoform of ITA, and thus a charge variant of ITA. ITA-2 has between 0-14 sialic acid residues and a pI or isoelectric point preferably ranging from about 5.0 to about 7.0.

As used herein, a "predetermined value" is a standardized value based on a control. For example, a predetermined value can be based on an amount of less acidic hCG isoforms that are present in a biological sample obtained from a pregnant woman who carries a normal fetus. In this embodiment of the invention, the presence of Down's syndrome is detected if the amount of less acidic hCG isoforms is greater than the predetermined value. In addition, in this embodiment, a "normal" fetus is a fetus that does not have trisomy 21. A normal fetus can be identified, for example, using amniocentesis.

Alternatively, the "predetermined value" can refer to a value that is based on an amount of less acidic isoforms in a biological sample obtained from a woman who carries a fetus with Down's syndrome. In this embodiment of the invention, the presence of Down's syndrome is detected if the amount of less acidic hCG isoforms is equal to or greater than the predetermined value.

As used herein, an "hCG isoform" is a hyperglycosylated variant of hCG, including, but not limited to, ITA and ITA-2.

As used herein, a "less acidic" isoform of hCG has a isoelectric point (pI) of greater than or equal to about 5.0. Preferably, a less acidic isoform of hCG has a pI of about 5.0-6.0, about 5.0-7.0, about 5.0-8.0, about 6.0-7.0, about 6.0-8.0, about 7.0-8.0, or higher than about 8.0. Most preferably, a less acidic isoform of hCG has a pI of about 5.0-7.0. For example, ITA-2 is a less acidic isoform of hCG.

As used herein, a "highly acidic" isoform of hCG has an isoelectric point (pI) of less than 5.0. Preferably, a highly acidic isoform of hCG has a pI of about 1.0-5.0, about 2.0-5.0, about 3.0-5.0, about 4.0-5.0, about 1.0-2.0, about 1.0-3.0, about 1.0-4.0, about 2.0-3.0, about 2.0-4.0, about 3.0-4.0. Most preferably, a highly acidic isoform of hCG has a pI of about 3.0-5.0. For example, ITA is a highly acidic isoform of hCG.

The term "amount" is used within the context of the analytical method used to measure the different hCG isoforms and may reflect a number, a concentration, etc., depending upon the analytical method chosen to measure the hCG isoforms.

The term "biological sample," as used herein, generally refers to urine, saliva, serum, plasma, tears, or amniotic fluid. However, any sample taken from a human that comprises hCG or an isoform of hCG can be used as a test or control sample. Preferably, the biological sample is urine, plasma, or serum.

The term "detecting" as used herein refers to identifying a fetus that has Down's syndrome or is at high risk for having Down's syndrome. For example, a pregnant woman carrying a Down's syndrome fetus as detected by a method of the invention can be considered a candidate for an invasive Down's syndrome test, such as amniocentesis.

In one aspect, the invention provides a method for detecting the presence or absence of Down's syndrome in a fetus of a pregnant woman comprising the steps of: (a) obtaining a biological sample from a pregnant woman; and (b) measuring the amount of less acidic hCG isoforms present in the biological sample, whereby the presence of Down's syndrome is detected if the amount of less acidic hCG isoforms is greater or equal to a predetermined value.

In one embodiment, the method further comprises measuring the amount of highly acidic hCG isoforms in the biological sample, and calculating a ratio of the amount of less acidic hCG isoforms to the amount of highly acidic isoforms of hCG, whereby the presence of Down's syndrome is detected if the ratio of less acidic to highly acidic isoforms of hCG is 1.5 or higher. A ratio of less acidic hCG isoforms to highly acidic hCG isoforms can be determined, for example, as described in the Examples provided herein.

In a particular embodiment, an amount of highly acidic hCG isoforms can be the amount of hCG or a mixture of hCG and highly acidic hCG isoforms present in a biological sample. In another embodiment, the amount of less acidic hCG isoforms comprises ITA-2. In yet another embodiment, the ratio of less acidic to highly acidic hCG is the ratio of ITA-2 to hCG, ITA-2 to ITA, or ITA-2 to a mixture of hCG and ITA.

In yet another embodiment, the ratio can be calculated by measuring an amount of highly acidic and less acidic hCG isoforms from protein fractions collected at various isoelectric point (pI) ranges from a biological sample. For example, protein fractions having pI ranges about 0.0-2.0, about 2.0-3.0, about 3.0-4.0, about 4.0-5.0, about 5.0-6.0, about 6.0-7.0, or about 8.0 and higher can be collected and the amount of hCG isoforms in each fraction, or combinations thereof, can be measured. A ratio can then be calculated by comparing the amount of hCG isoforms in one or more fractions above pI 5.0 with the amount of hCG isoforms in one or more fractions below pI 5.0. In this embodiment, the presence of a Down's syndrome fetus can be detected when the ratio of less acidic hCG isoforms (hCG isoforms in one or more fractions above pI 5.0) to highly acidic hCG isoforms (hCG isoforms in one or more fractions below pI 5.0) is greater than or equal to about 1.5.

Alternatively, fractions from various pI ranges can be pooled and the concentration of hCG isoforms in a highly acidic pool can be compared with the concentration of hCG isoforms in a less acidic pool. Preferably, as described in the Examples below, fractions from pI about 3.0-5.0 are pooled and fractions from pI 5.0-7.0 are pooled, the amount of hCG isoforms in each pool is measured, and the ratio of hCG isoforms in the 5.0-7.0 fraction to hCG isoforms in the 3.0-5.0 fraction is determined. A ratio of 1.5 or higher indicates the presence of Down's syndrome.

An isoelectric point (pI) can be determined using standard methods known in the art, such as isolectric focusing as described herein.

In still another embodiment, the presence or absence of a Down's syndrome fetus can be detected by directly or indirectly measuring the amount of ITA-2 in a biological sample and comparing the amount of ITA-2 with an amount of ITA-2 present in a control sample or control samples, wherein the control sample is obtained from a pregnant woman (or group of at least two pregnant women) that carries a normal fetus or from a pregnant woman (or group of at least two pregnant women) that carries a Down's syndrome fetus. In this embodiment, if the amount of ITA-2 in the test sample is greater than the amount of ITA-2 in the control sample(s) obtained from a pregnant woman (or group of at least two pregnant women) carrying a normal fetus, the presence of Down's syndrome is detected. Alternatively, the presence of Down's syndrome is detected if the amount of ITA-2 is equal to or greater than the amount of ITA-2 in the sample obtained from a pregnant woman (or group of at least two pregnant women) carrying a fetus with Down's syndrome.

ITA-2 can be directly measured, for example, using anti-ITA-2 antibodies in an immunoassay, such as a Western blot or ELISA. Anti-ITA-2 antibodies can be generated as described herein. ITA-2 can be indirectly measured, for example, using an hCG capture antibody that binds hCG and various hCG isoforms, such as ITA and ITA-2, followed by either carbohydrate analysis, which will distinguish ITA-2 from ITA by variations in sialic acid content, or by removing normal hCG and ITA using anti-hCG antibodies and anti-ITA antibodies and quantifying remaining protein, which would consist of ITA-2 protein. Alternatively, ITA-2 can be indirectly measured, for example, using a capture antibody that recognizes only hyperglycosylated hCG, which would recognize both ITA and ITA-2, and then distinguishing ITA-2 by removing ITA from the sample using an antibody that specifically recognizes ITA. An example of a monoclonal antibody that recognizes ITA is B-152, described in U.S. Pat. No. 6,339,143, relevant portions of which are incorporated by reference herein. ITA-2 is discussed in Sutton and Cole, *Prenatal Diagnosis*, 24:194-197 (2004) and *Down Syndrome News*, 10:32 (2003), relevant portions of which are incorporated by reference herein.

The methods of the invention can be used alone or in combination with any known Down's syndrome screening test, including, but not limited to, a triple screen test (combination of maternal age with serum measurements of hCG, α-fetoprotein (AFP), and unconjugated estriol), unconjugated and/or conjugated estriol measurements, hCG assays, β-core fragment analyses, free β-subunit or free α-subunit analyses, PAPP-A or CA125 analyses, α-fetoprotein analyses, inhibin assays, observations of fetal cells in serum, and ultrasound, which will increase the sensitivity and decrease the number of false positives of known tests for Down's syndrome.

The methods of the invention can be used to screen a biological sample collected during the first, second, or third trimester of pregnancy. In addition, the methods of the invention can be combined with any known Down's syndrome test during the first, second, or third trimester of pregnancy. For example, the methods of the invention can be combined with a triple screen test plus ITA screen during the second trimester, or with PAPP-1 and hCG free-β subunit and ITA screens in the first trimester.

In yet another embodiment, the methods of the invention can be used alone or in combination with other Down's syndrome screening methods to identify candidates for amniocentesis. In this embodiment, a pregnant woman providing a biological sample in which Down's syndrome is detected using a method of the invention or a method of the invention in combination with one or more known Down's syndrome screening methods can be selected for amniocentesis.

The amount of highly acidic and less acidic hCG isoforms in a biological sample can be determined using any method known in the art, including, but not limited to, immunoassays using antibodies specific for various hCG charge isoforms, isoelectric focusing, carbohydrate analysis, matrix assisted laser desorption/ionization (MALDI), or some combination thereof. For example, highly acidic and less acidic hCG isoforms can be distinguished in a biological sample by first preparing the sample for isoelectric focusing by diluting the sample with ampholytes and separating the proteins in the sample by charge using, for example, a Rotofor® Cell (Bio-Rad, Hercules, Calif.). Then, fractions of proteins can be collected at particular isoelectric point (pI) ranges, and hCG isoforms in each fraction of various pI ranges can be quantitatively determined.

Any assay that functions to qualitatively or quantitatively determine variations in sample concentrations of hCG from normal levels, and/or detects hCG isoforms in the sample's gonadotropin population can be employed in the practice of the invention. A direct assay, such as an immunoassay using antibodies that recognize hCG or specific hCG isoforms, is preferred, but other exemplary assays can involve lectins that assay for carbohydrate moieties or any other fingerprinting technique including qualitative or quantitative carbohydrate composition analysis, chromatography, chemical or electrophoresis or isoelectric focusing tests, among others, or any other methods that detect glycosylation variants of hCG, and/or antibodies to hyperglycosylated or carbohydrate-variant hCG. Such assays are described in the art.

Immunoassays that can be used to detect hCG or hCG isoforms include, but are not limited to, assays employing specific antibodies to hCG, ITA, or ITA-2, and assays employing nonspecifically defined antibodies obtained by blind injections of a less acidic hCG isoform, such as ITA-2, into test animals using standard methods. Antibodies to hCG and hCG isoforms, such as ITA and ITA-2, can be generated by standard means as described, for example, in "Antibodies: A Laboratory Manual" by Harlow and Lane (Cold Spring Harbor Press, 1988), which is hereby incorporated by reference.

For example, a monoclonal anti-ITA-2 antibody can be generated by immunizing a mouse with recombinant ITA-2, purified ITA-2, ITA pre-treated with neuramimidase, or a cell expressing recombinant ITA-2, purified ITA-2, or ITA pre-treated with neuramimidase. Once an immune response is detected, e.g., antibodies specific for ITA-2 are detected in the mouse serum, the mouse spleen is harvested and splenocytes are isolated. The splenocytes are then fused by well-known techniques to any suitable myeloma cells, for example, cells from cell line SP20 available from the American Type Culture Collection (ATCC). Hybridomas are selected and cloned by limited dilution. The hybridoma clones are then assayed by methods known in the art for cells that secrete antibodies capable of binding ITA-2. Ascites fluid, which generally contains high levels of antibodies, can be generated by immunizing mice with positive hybridoma clones.

Any type of fusion phage, monoclonal, or polyclonal antibodies can be used in immunoassays of the invention, so long as the antibodies can be used in a reproducible fashion as markers for various hCG isoforms, particularly less acidic hCG isoforms such as ITA-2, or as measures of the different levels of hCG isoforms observed in normal and variant populations.

In one embodiment, an amount of hCG or a hyperglycoslyated hCG isoform can be measured using a capture antibody followed by a labeled secondary antibody using a strategy as described, for example, in U.S. Pat. No. 6,429,018 (which is hereby incorporated by reference). U.S. Pat. No. 6,429,018 teaches the B152 antibody that recognizes nicked hyperglycosylated hCG but does not detect normal hCG. A labeled secondary antibody useful in a method of the invention (for example, as taught by U.S. Pat. No. 6,339,143 can be, for example, an anti-hCG antibody, β-core fragment, α-subunit, and/or β-subunit, providing assay with polypeptide specificity. The label on the secondary antibody can comprise any chemical, radioactive, lanthanide, colored dye, or genetic tag used in enzyme-linked immunosorbent assays (ELISAs), Western blots, and other sensitive and specific immunoassays and immunoradiometric assays using known methodology. These include conjugating the antibody with horseradish peroxidase or alkaline phosphatase that are easily measurable, typically using colorimetric, fluorometric or luminescent substrates. Genetic labels include firefly luciferase, employed because luciferase produces a bioluminescent molecule when incubated with its substrate, luciferin.

In other embodiments, hCG peptide-specific antibody can be used as a capture antibody, and an antibody specific to hyperglycosylated or carbohydrate-variant hCG and/or an abnormal carbohydrate portion thereof can be used as the secondary labeled antibody in an immunoassay such as those described above. Competitive immunoassays employing antibodies to specific hCG isoforms can also be employed to competitively detect hCG isoforms. For example, an antibody that binds non-specifically to both ITA and ITA-2 can be used to immunoprecipitate total ITA present in a sample, followed by a second immunoprecipitation step in which ITA-specific antibodies are used to separate ITA from ITA-2. The remaining ITA-2 protein can be quantified using standard methods, such as a Bradford protein assay. Alternate embodiments using concanavalin A or other carbohydrate-specific lectin can be used in place of the capture antibody or labeled antibody. Alternatively, prior to an immunoassay, a lectin or chromatographic method can be used to extract carbohydrate-variant hCG isoforms, including ITA and/or ITA-2, from a biological sample or from a fraction that was separated or pooled according to pI range. These methods are all well known in the art.

Carbohydrate analyses include qualitative observations of differences in physical properties between normal and Down's syndrome hCG populations, carbohydrate identification using plant lectins specific to the variant carbohydrate portion of hCG isoforms found in Down's syndrome pregnancies obtained by standard lectin screening methods, or any other fingerprinting technique including qualitative or quantitative carbohydrate composition analyses. See, for example, U.S. Pat. No. 6,429,018, which is incorporated by reference herein.

In certain embodiments, hCG or hCG isoforms can be purified from biological samples prior to separating the hCG isoforms by charge distribution. Any method for purifying hCG can be used. For example, antibodies specific for hCG or specific hCG isoforms can be used to isolate hCG or hCG isoforms from a biological sample. A purified hCG protein fraction can be subjected to isoelectric focusing or any other method described herein to determine the amount of highly and less acidic isoforms present in the samples having various pI values or ranges. Purified hCG and hCG isoforms from control or test samples can be stored under appropriate conditions, such as those described, for example, in Cole et al., 1999, *Clinical Chem.* 45:2109-2119, which is hereby incorporated by reference.

Unless otherwise required by context, singular terms referred to herein shall include pluralities and plural terms shall include the singular.

EXAMPLE

The following example, including the experiments conducted and results achieved is provided for illustrative purposes only and are not to be construed as limiting the invention.

Preparative Isoelectric Focusing of Urine Samples from Pregnant Women Carrying Down Syndrome or Normal Fetuses Ten urine samples were collected from different women all at 16-18 weeks of gestation. In all 10 cases, trisomy 21 was confirmed. Additionally, 10 control urine samples from normal pregnancies, at the same gestational age, were collected. Accrued samples were stored at −80° C. until use.

The urine samples were each separated by preparative isoelectric focusing using a Rotofor® apparatus (Bio-Rad, Richmond Calif.) with a mini-Rotofor®cell, a Bio-Rad Power-Pac 3000 power supply and a circulating refrigeration bath (Neslab, Portsmouth, N.H.). The Rotofor® cell was pre-focused using 1.5% ampholytes, pI range 3-7, at constant power (15 W) for 1 hour at 4° C. (refrigerated circulating bath). Samples were added to the pre-focused mixture per manufacturer's instructions, and the mixture was then focused at constant power (15 W) at 4° C. until voltage stabilization was achieved. After an additional 30 minutes, to allow for complete separation, power was removed and twenty 1 ml fractions were collected. The pH of each of the 20 fractions was determined with a microelectrode to determine the corresponding isoelectric point (pI). Fractions were analyzed using an ITA assay as described previously (Cole et al., 1999, $Clin\ Chem$ 45:2109-19). Fractions were then pooled according to pI ranges of 3-4, 4-5, 5-6, and 6-7.

Figure 2:
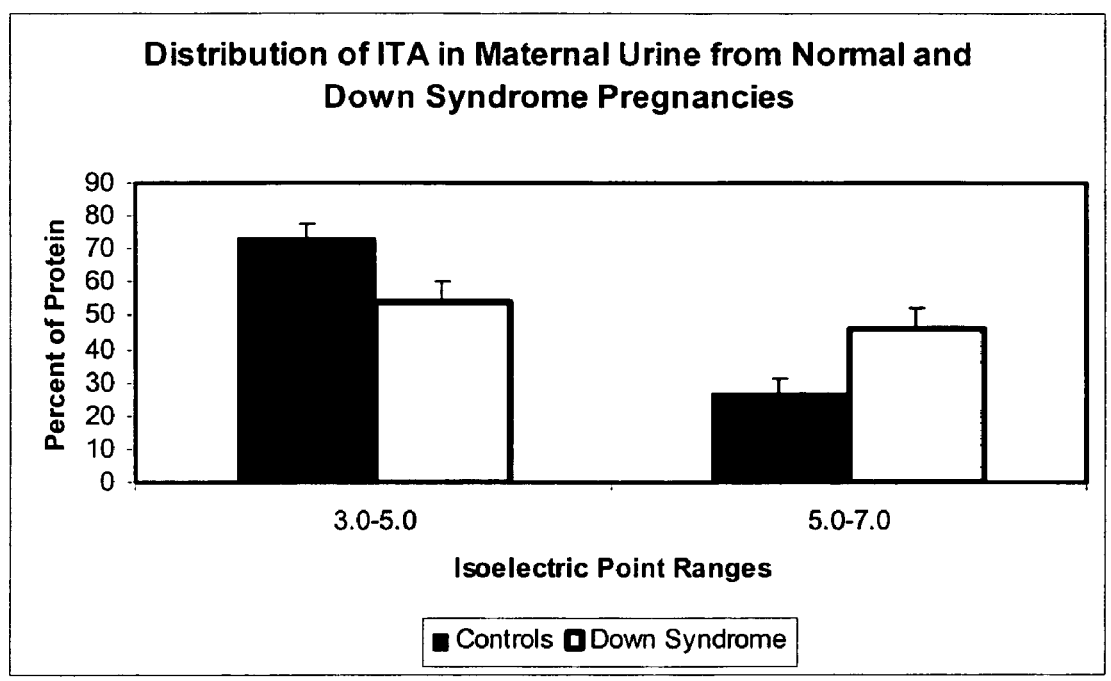
FIG. 2 shows the charge distribution of ITA from normal and Down syndrome urine samples in the more acidic pI range of about 3-5 and the less acidic pI range of about 5-7. Grouping in these two more and less acidic pI ranges clearly illustrates the charge variability that exists at the less acidic end of the profile.

As shown in FIG. 1, a difference in charge profiles was observed. The distribution of ITA immunoreactivity in control samples was 38.0±6.1%, 35.3±7.2%, 14.5±2.3%, and 12.2±2.9% in pI ranges 3-4, 4-5, 5-6, and 6-7 respectively. The distribution of ITA immunoreactivity in Down's syndrome samples was 21.7±3.1%, 32.7±5.0%, 26.5±5.4%, and 19.1±4.5% in pI ranges 3-4, 4-5, 5-6, and 6-7 respectively. As shown in FIG. 2, a significant difference was seen with the charge distribution was grouped into the two less-acidic and more-acidic pI ranges of 3-5 and 5-7 (P=0.02). For the more-acidic pI range of 3-5, 73.3±4.3% of the control samples and 54.4±6.3% of the Down's syndrome samples focused in that range. For the less-acidic pI range of 5-7, 26.7±4.3% of the control samples and 45.6±6.3% of the Down's syndrome samples focused in that range.

To illustrate that the sialic acid content caused the variation in charge distribution between the normal and Down syndrome samples, standard ITA (from JEG-3 cells) was treated with two units of neuramimidase (type X, Sigma) and incubated at 37° C. for 24 hours to remove terminal sialic acid residues. This sialic acid deficient preparation was focused on the Rotofor® apparatus as described above, and the resulting fractions were measured for pH, assayed for ITA, and pooled in pI ranges 3-4, 4-5, 5-6, and 6-7. In addition the standard ITA preparation was also focused in the same way for comparison to the desialylated preparation.

Figure 3:
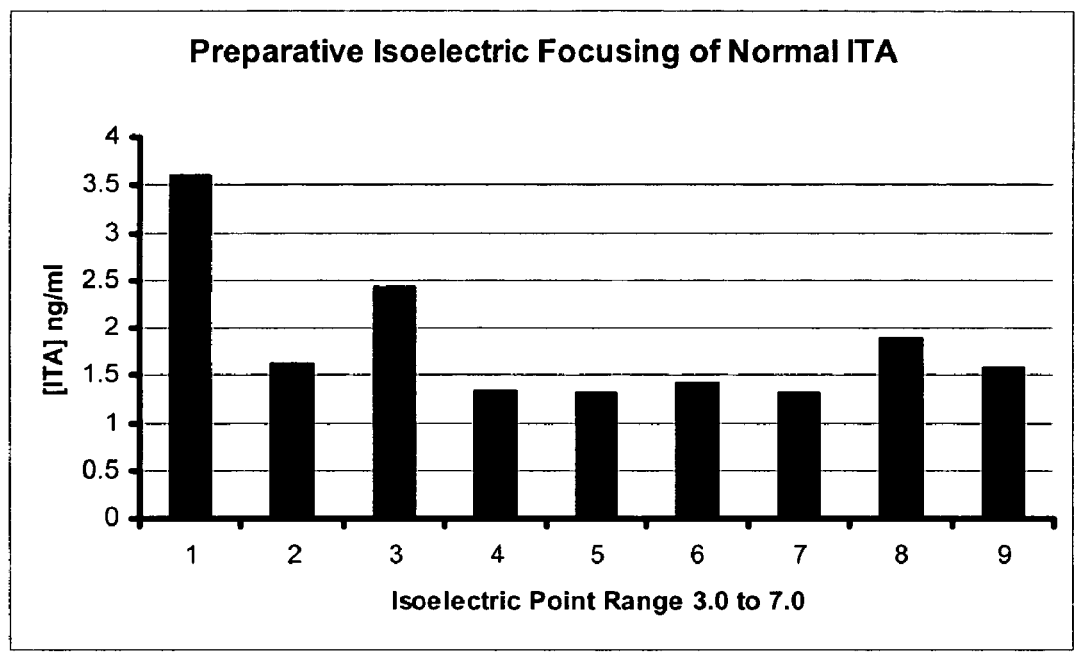
FIG. 3 shows the charge distribution of the normal ITA standard.
Figure 4:
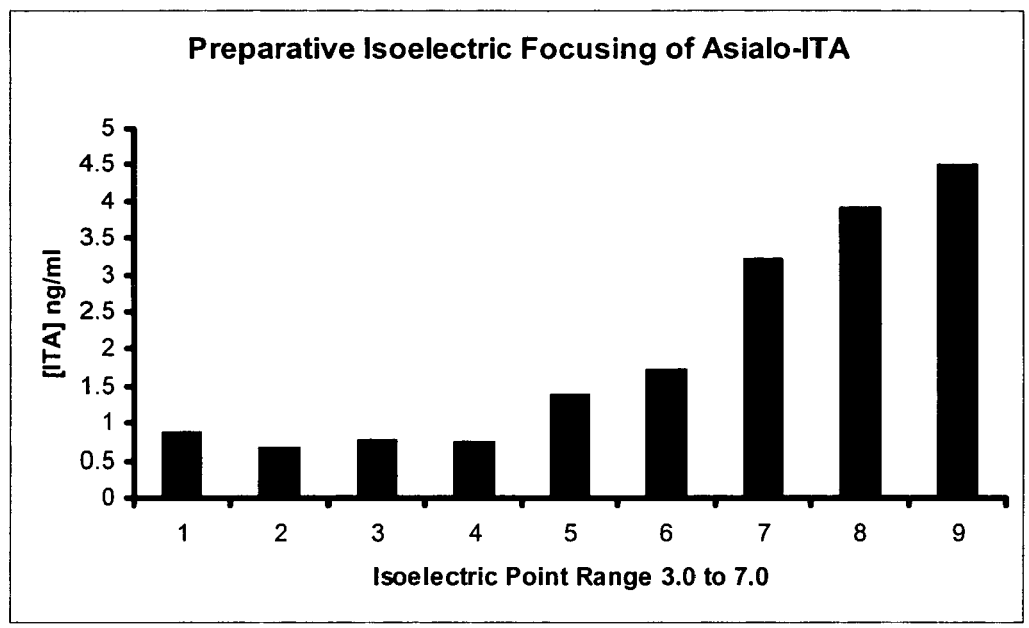
FIG. 4 shows the charge distribution of the ITA standard after treated with neuramimidase to remove terminal sialic acid residues.

As shown in FIG. 3, a wide distribution of the protein was observed across the ranges between pI 3-7. After the ITA standard was treated with neuramimidase, the sialic acid deficient, or desialylated-ITA, preparation was then separated by preparative isoelectric focusing. As shown in FIG. 4, a significant proportion (76%) of the desialylated ITA focused in the less-acidic range of pI 5-7, whereas only 38% of the normal standard ITA focused in that range. The majority of the protein focused in the same range where the bulk of the ITA-2 protein focused, and the charge of the desialylated ITA closely resembled that of ITA-2.

The results of these experiments demonstrated that raised ITA levels in Down's syndrome pregnancies was largely due to an increase in less acidic isoforms of ITA (ITA-2) compared to normal karyotype pregnancies. When maternal urine from normal and Down's syndrome pregnancies were compared, the charge profiles showed a significant difference (P=0.02) in more-acidic and less-acidic isoforms.

Thus, as demonstrated by these experiments, most of the increase in ITA that occurs in Down syndrome cases is due to a charge variant of ITA, ITA-2, which is deficient in sialic acid.

It should be understood that the foregoing disclosure emphasizes certain specific embodiments of the invention and that all modifications or alternatives equivalent thereto are within the spirit and scope of the invention as set forth in the appended claims.

We claim:

1. A method for detecting the presence or absence of Down's syndrome in a fetus of a pregnant woman to be tested comprising the steps of:
   a. obtaining a urine sample from said pregnant woman to be tested;
   b. determining a percentage of invasive trophoblast antigen (ITA) having a pI ranging from 5.0 to 7.0 present of a total amount of ITA having a pI ranging from 3.0 to 7.0 in the urine sample; and
   c. comparing the percentage obtained in step b with a predetermined value obtained by determining a percentage of ITA having a pI ranging from 5.0 to 7.0 of a total amount of ITA having a pI ranging from 3.0 to 7.0 in sample(s) from at least ten pregnant woman carrying a normal fetus of the same gestational age as said fetus of said pregnant woman to be tested, wherein said percentage obtained in step b which is at least 1.5 times the predetermined value is predictive of Down's syndrome.

2. The method according to claim 1 wherein said percentage obtained from step b which is at least 1.7 times the predetermined value is predictive of Down's syndrome.

* * * * *